US012605262B2

(12) United States Patent　　　　(10) Patent No.:　US 12,605,262 B2

Pilosof et al.　　　　　　　　　　(45) Date of Patent:　　Apr. 21, 2026

---

(54) INFLATABLE LIMB PROSTHESIS

(71) Applicant: Y. D. GAPIM LTD., Rishon Lezion (IL)

(72) Inventors: Israel Pilosof, Beer Yaakov (IL);
Yehuda Pilosof, Rishon Lezion (IL)

( * ) Notice: Subject to any disclaimer, the term of this patent is extended or adjusted under 35 U.S.C. 154(b) by 0 days.

(21) Appl. No.: 18/964,742

(22) Filed: Dec. 2, 2024

(65) Prior Publication Data

US 2025/0090352 A1　　Mar. 20, 2025

Related U.S. Application Data

(63) Continuation-in-part of application No. 16/701,302, filed on Dec. 3, 2019, now abandoned.

(30) Foreign Application Priority Data

Apr. 16, 2019　　(IL) ......................................... 266074

(51) Int. Cl.
　　*A61F 2/74*　　　　(2006.01)
　　*A61F 2/70*　　　　(2006.01)
　　*A61F 2/78*　　　　(2006.01)
　　*A61F 2/80*　　　　(2006.01)
　　　　　　　(Continued)

(52) U.S. Cl.
　　CPC ................ *A61F 2/80* (2013.01); *A61F 2/748* (2021.08); *A61F 2/7843* (2013.01); *A61F 2002/5012* (2013.01); *A61F 2002/5026* (2013.01); *A61F 2002/5027* (2013.01); *A61F 2002/5032* (2013.01); *A61F 2002/704* (2013.01); *A61F 2002/707* (2013.01); *A61F 2002/7655* (2013.01); *A61F 2002/805* (2013.01)

(58) Field of Classification Search
　　CPC ... A61F 2/602; A61F 2/7843; A61F 2002/707

USPC .......................................................... 623/37
　　See application file for complete search history.

(56) References Cited

U.S. PATENT DOCUMENTS

| 2016/0228266 A1 | 8/2016 | Alley |
| 2018/0020973 A1 | 1/2018 | Hurley |
| 2022/0023072 A1* | 1/2022 | Engelbart ................. A61F 2/74 |

FOREIGN PATENT DOCUMENTS

| GB | 698150 A | 10/1953 | |
| KR | 10-2434955 B1 * | 8/2022 | ............... A61F 2/78 |
| WO | 2008098053 A1 | 8/2008 | |
| | (Continued) | | |

*Primary Examiner* — David H Willse

(74) *Attorney, Agent, or Firm* — AlphaPatent Associates Ltd.; Daniel J. Swirsky

(57)　　　　　　ABSTRACT

A limb prosthesis including a socket having an inner cavity configured for disposal therein of a limb stump of a user, and a mechanism for changing an inner diameter of the inner cavity by a remote control, where the inner diameter includes a lining disposed within the cavity, having between fifteen and sixty of only longitudinal inflatable cells where each of the cells is situated immediately adjacent to two other of the cells such that no intervening element aside from a shared border is provided between two such immediately adjacent cells, thereby diminishing blood flow blockage in the limb stump, and a pump assembly, for inflating and deflating the inflatable lining to a desired air pressure set by a user or by a controller, the remote control being in data communication with the pump assembly, for instructing the pump assembly to inflate or deflate the lining to the desired air pressure.

13 Claims, 9 Drawing Sheets

(51) Int. Cl.
    *A61F 2/50*         (2006.01)
    *A61F 2/76*         (2006.01)

(56)              References Cited

FOREIGN PATENT DOCUMENTS

WO         2013049847 A2    4/2013
WO    WO 2017/221019 A1 *  12/2017  ............... A61F 2/78

* cited by examiner

10

11

13

12

INFLATABLE LIMB PROSTHESIS

FIELD

The invention relates to the field of limb prostheses.

BACKGROUND

In medicine, prosthesis is an artificial device that replaces a missing body part, which may be lost through trauma, disease, or congenital conditions. Prosthetics are intended to restore the normal functions of the missing body part.

FIG. 1 schematically illustrates a foot prosthesis, according to the prior art.

The prosthesis comprises a socket 11, connected to a prosthetic foot 12 by a joint pipe 13.

The prosthesis comprises also a lining disposed inside the socket 11. The lining is not seen in this figure.

While the socket 11 is made of "hard" material, the lining is made of "soft" material, such as sponge and gel, in order to soften the contact of the user stump (the distal end of a limb left after amputation) with the socket 11.

FIG. 2 schematically illustrates user using a foot prosthesis, according to the prior art.

In this figure is seen also a sock 15, worn on the stump 14. The sock adds softness to the contact of the stump with the prosthesis. The dashed line 14 illustrates the user's foot stump hidden behind the prosthesis socket.

FIG. 3 schematically illustrates steps in mounting a prosthesis, according to the prior art.

In step (a) there is shown a bare stump 14;

In step (b) the user wears one or more socks 15 on the stump 14;

In step (c) the user wears a lining 16 on sock 15; and

In step (d) the user wears a socket 11 on the lining.

During the day, the stump may change its size, i.e., to shrink or to expand. As such, the prosthesis socket loses its correct fit to the user's stump. In order to overcome this obstacle, the user may wear during the day additional or less sock(s), an action which may be embarrassing and inconvenient.

U.S. Pat. No. 5,405,405A discloses a composite socket member for use with a prosthetic appliance for a residual limb which comprises an outer socket which defines an inner cavity generally conforming to the outer surface of a residual limb, an inner socket which defines an inner cavity and being adapted to receive the residual limb, with the inner socket conforming to the shape of the outer socket and when nested within the cavity of the outer socket defines an air space between the inner surface of the outer socket and the outer surface of the inner socket and an inflatable bladder being disposed between the inner surface of the outer socket and the outer surface of the inner socket. The inner socket contains at least one opening through its side wall at a preselected weight-bearing location whereby upon inflation of the bladder, pressure is applied by the bladder through the side wall opening against the preselected weight-bearing location of the residual limb to control the movement and rotation stability of the prosthetic appliance.

EP2327378A1 discloses a cap (13) for the application of a limb prosthesis, in particular a prosthesis for a lower limb, comprises a dual membrane structure, with a first inner membrane (15) and a second outer membrane (13), defining a sealed hollow space (19). The inner membrane defines a volume (18) for seating the limb stump (M) and the outer membrane (17) defines a surface of contact and adhesion to the socket (3) of the prosthesis (1). Thus, the publication shows a single hollow space 19 and the protrusions of the surface 17 that confines the hollow space 17 turns outwards.

All the methods described above have not yet provided satisfactory solutions to the problem of adjusting a prosthesis pressure on a limb stump.

SUMMARY

In one aspect, the invention is directed to a limb prosthesis, comprising a socket comprising an inner cavity configured for disposal therein of a limb stump of a user, a means for changing an inner diameter of the inner cavity by a remote control, wherein the means for changing the inner diameter comprises a lining (16) disposed within the cavity, the lining comprising between fifteen to sixty of only longitudinal inflatable cells wherein each of the cells is situated immediately adjacent to two other of the cells such that no intervening element aside from a shared border is provided between two such immediately adjacent cells, wherein all of the inflatable cells are configured to inflate simultaneously towards a limb stump disposed in the prosthesis, wherein inflation or deflation of the inflatable cells changes the inner diameter of the cavity, providing an adjustable space between the cells and the limb stump, thereby diminishing blood flow blockage in the limb stump, and a pump assembly (19), for inflating and deflating the inflatable lining (16) to a desired air pressure set by a user or by a controller, wherein the remote control (17) being in data communication with the pump assembly (19), for instructing the pump assembly to inflate or deflate the lining (16) to the desired air pressure.

The limb prosthesis may further comprise a pressure sensor and a controllable valve, for allowing inflating and deflating the lining (16) to a desired pressure.

The limb prosthesis may further comprise a circuitry adapted to retain constant pressure in the lining.

According to embodiments of the invention, the remote control (17) is a smartphone, thereby allowing a user to change the pressure of the lining without attracting attention of nearby individuals.

According to embodiments of the invention, the data communication is wired.

According to embodiments of the invention, the data communication is wireless.

The limb prosthesis may further comprise means for manually deflating the lining, thereby allowing deflating the lining in the case of an operational fault.

According to embodiments of the invention, the means for changing an inner size of a socket of the limb prosthesis by a remote control are pneumatic.

According to embodiments of the invention, the means for changing an inner size of a socket of the limb prosthesis by a remote control are mechanical.

According to embodiments of the invention, the pump assembly (19) is disposed in a joint pipe (13) connecting the socket (11) with a prosthetic foot (12).

According to embodiments of the invention, wherein the pump assembly (19) is disposed in a prosthetic foot (12) of the limb prosthesis.

BRIEF DESCRIPTION OF THE DRAWINGS

Embodiments, features, and aspects of the invention are described herein in conjunction with the following drawings in which.

It should be understood that the drawings are not necessarily drawn to scale.

DETAILED DESCRIPTION

The invention will be understood from the following detailed description of embodiments, which are meant to be descriptive and not limiting. For the sake of brevity, some well-known features, methods, systems, procedures, components, circuits, and so on, are not described in detail.

Figure 1:
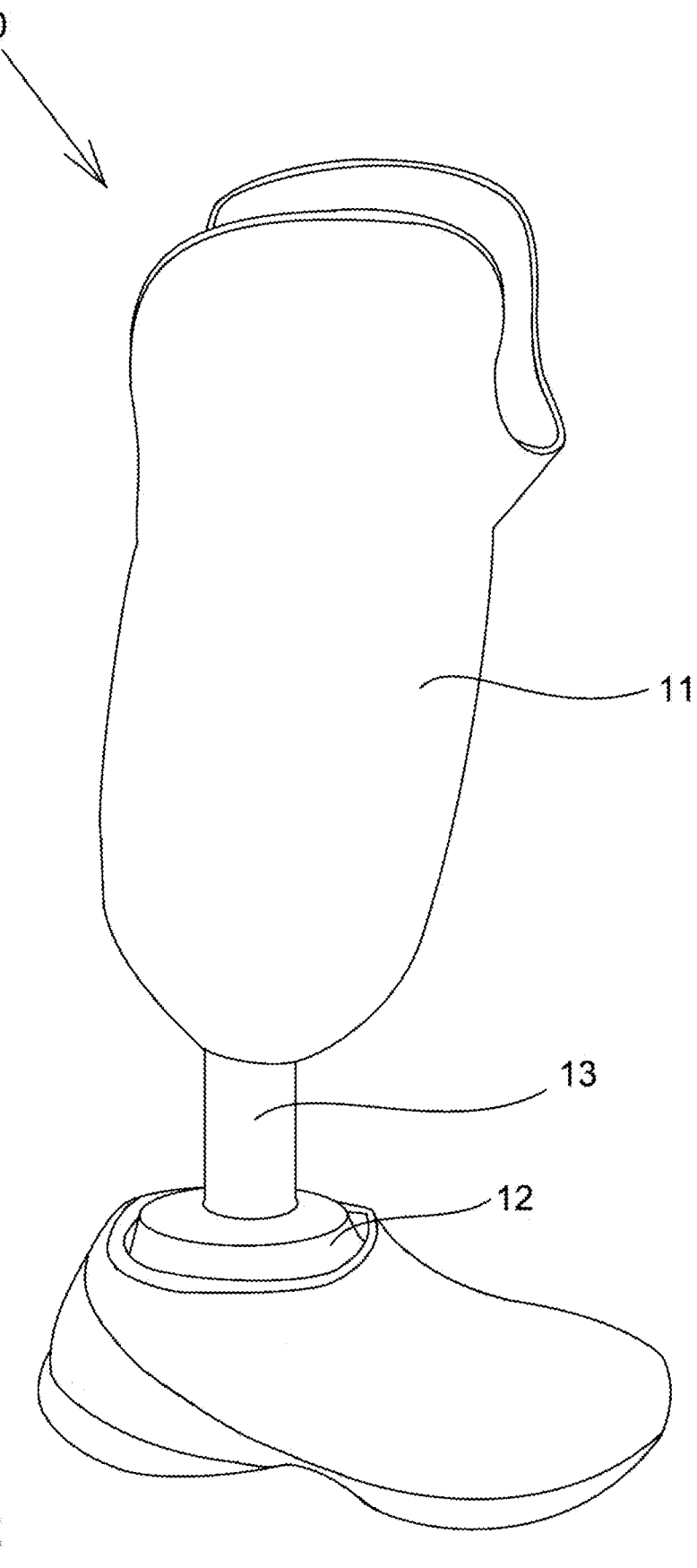
FIG. 1 schematically illustrates a foot prosthesis, according to the prior art.
Figure 2:
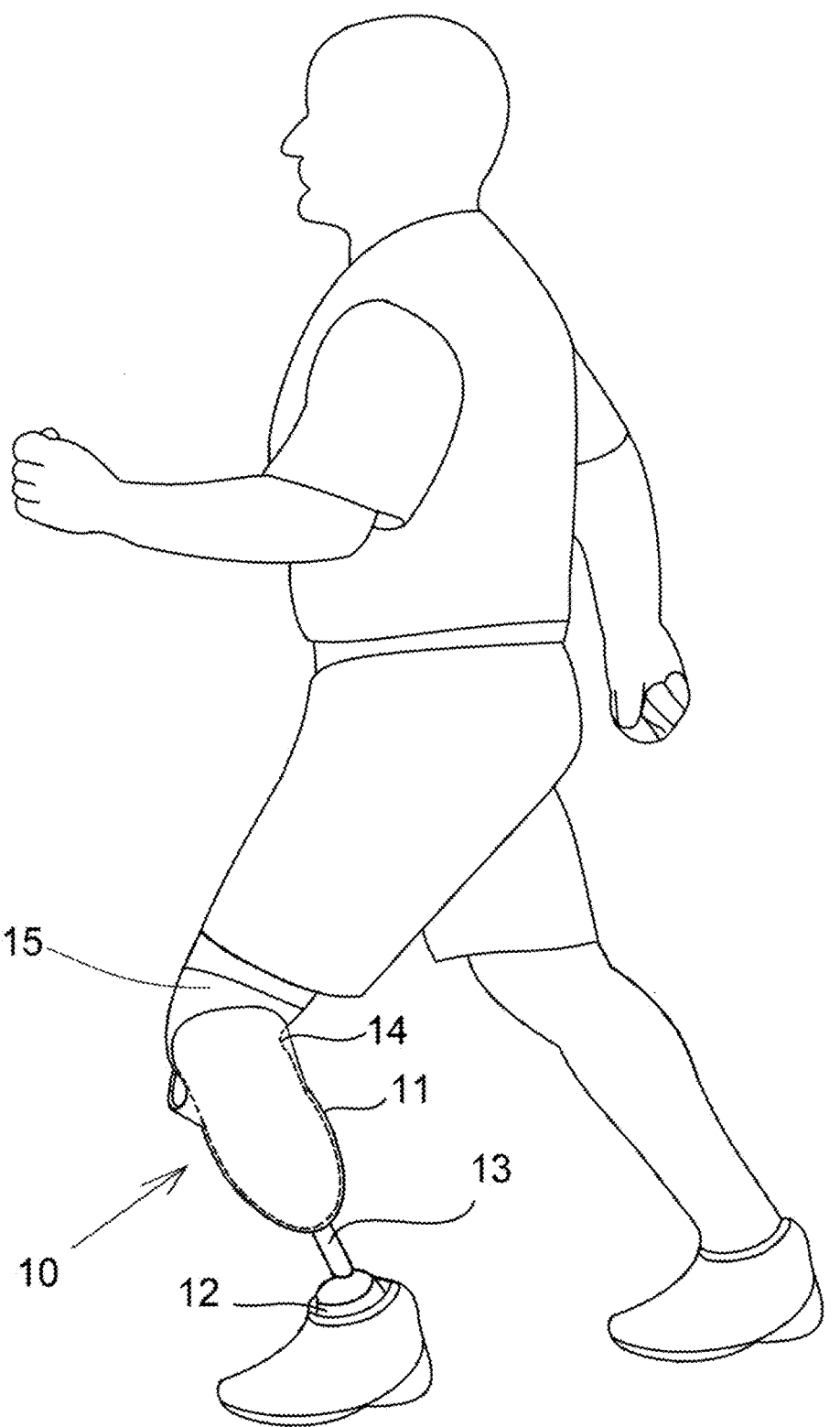
FIG. 2 schematically illustrates user using a foot prosthesis, according to the prior art.
Figure 3:
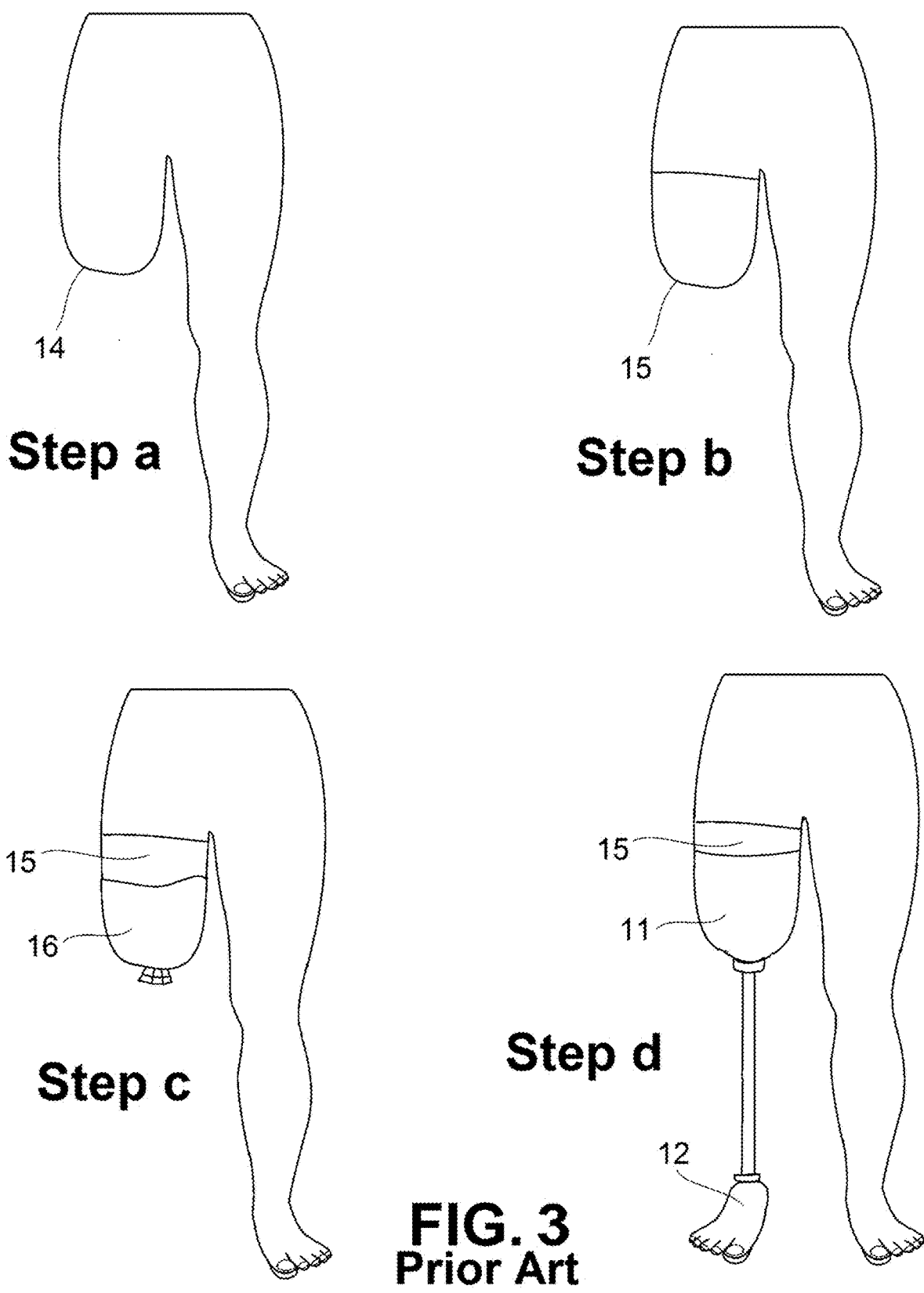
FIG. 3 schematically illustrates steps in mounting a prosthesis, according to the prior art.
Figure 4:
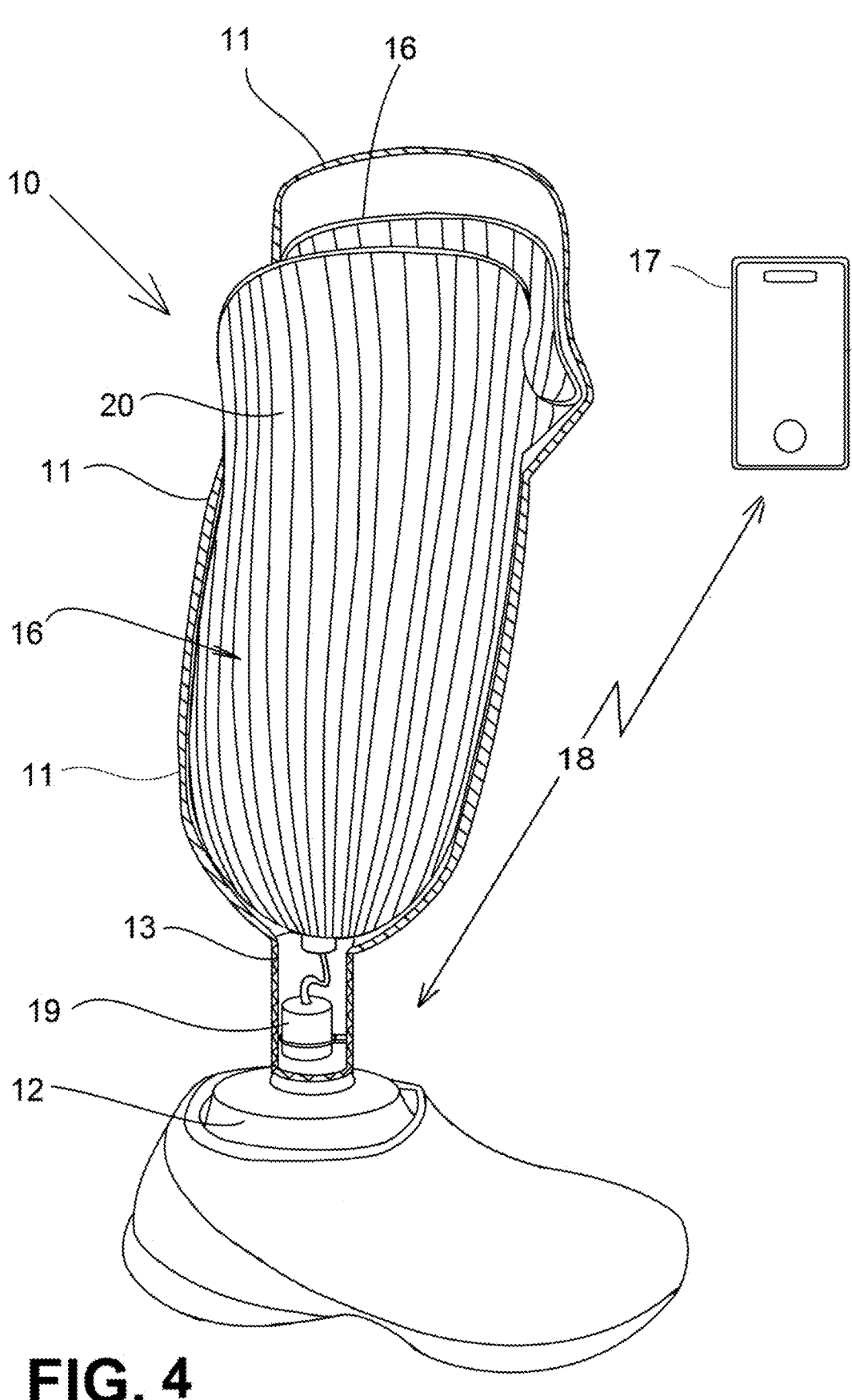
FIG. 4 schematically illustrates a prosthesis, according to one embodiment of the invention.

FIG. 4 schematically illustrates a prosthesis, according to one embodiment of the invention.

In this figure the socket 11 is longitudinally sectioned, for showing the parts of the prosthesis which are disposed inside the socket 11.

The prosthesis comprises an inflatable lining 16, inflatable by a pump assembly 19, and a pressure sensor (not shown) for measuring the air pressure inside the inflatable lining 16. Despite of the fact that the inlet from the pump assembly to the lining is drawn in FIG. 4 from the bottom of the lining, it should be noted that the inlet can be positioned elsewhere in the lining.

The pump assembly may be disposed in an unused space of the prosthesis, such as the prosthetic foot 12, and the joint pipe 13.

A communication assembly (not shown in this figure) disposed at the prosthesis has data connection with the pump assembly. The communication assembly communicates with the remote control 17 (preferably via wireless communication 18 such as Wi-Fi). The remote control may be in a form of a smartphone which executes a tailored application.

The user interface of the remote control 17 provides means through which a user can set the desired pressure inside the inflatable lining 16, to deflate (i.e., to release the air trapped inside the lining) the lining 16, and so on.

The prosthesis uses a controller (not illustrated in this figure), which instructs the pump assembly to inflate the inflatable lining 16 to a desired pressure. The desired pressure is set by a user via the remote control 17.

Alternatively, the user may order the pump assembly to inflate the lining, and when he feels that the air pressure is adequate, he may stop the inflating. The prosthesis may retain this pressure until the user instructs the controller to release the pressure (e.g., via a valve).

During the day the pressure inside the inflated lining may decrease due to leg contraction and air leakage. The controller may be set to re-inflate the inflatable lining 16 up to the pressure that has been set by the user.

The controller may reside in the prosthesis 10 or in the remote control 17. The controller may track the pressure inside the inflatable lining, and once it decreases, the controller can instruct the pump assembly to re-inflate the lining 16 to the set up pressure.

Figure 5:
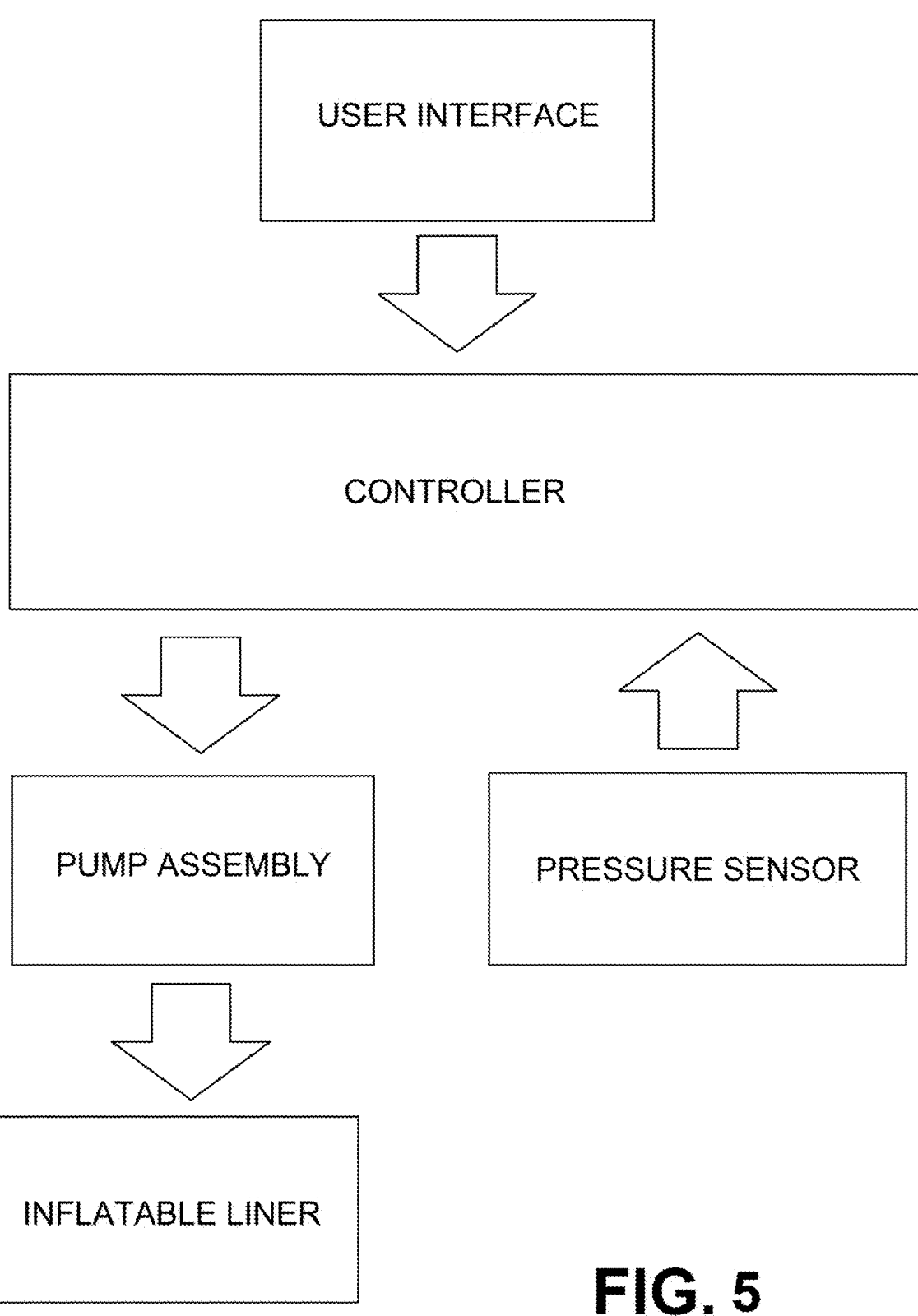
FIG. 5 is a block diagram schematically illustrating the dataflow in a prosthesis, according to one embodiment of the invention.

FIG. 5 is a block diagram schematically illustrating the dataflow in a prosthesis, according to one embodiment of the invention.

For example, the user instructs the pump assembly to inflate the inflatable lining, and then to keep this pressure inside the lining.

The user sets the operation mode by the user interface, which sends the setup information to the controller via wireless communication means.

The controller instructs the pump assembly to inflate the inflatable lining, and while the lining is inflated, the pressure inside the lining is measured.

From the moment the user has instructed (via the user interface) the pump assembly to stop inflating, the controller acquires the pressure inside the lining (by reading the pressure sensor). From this stage the controller alternately or continuously acquires the air pressure inside the inflated lining (by reading the pressure sensor), and if the pressure has been changed from the one that has been set, e.g., by 3%, the controller instructs the pump assembly to inflate/deflate the lining to the pressure that has been set. The deflation is carried out by releasing air from the lining (e.g., by a controllable valve).

As mentioned above, the controller may reside at the prosthesis side, or at the remote control side.

Figure 6A:
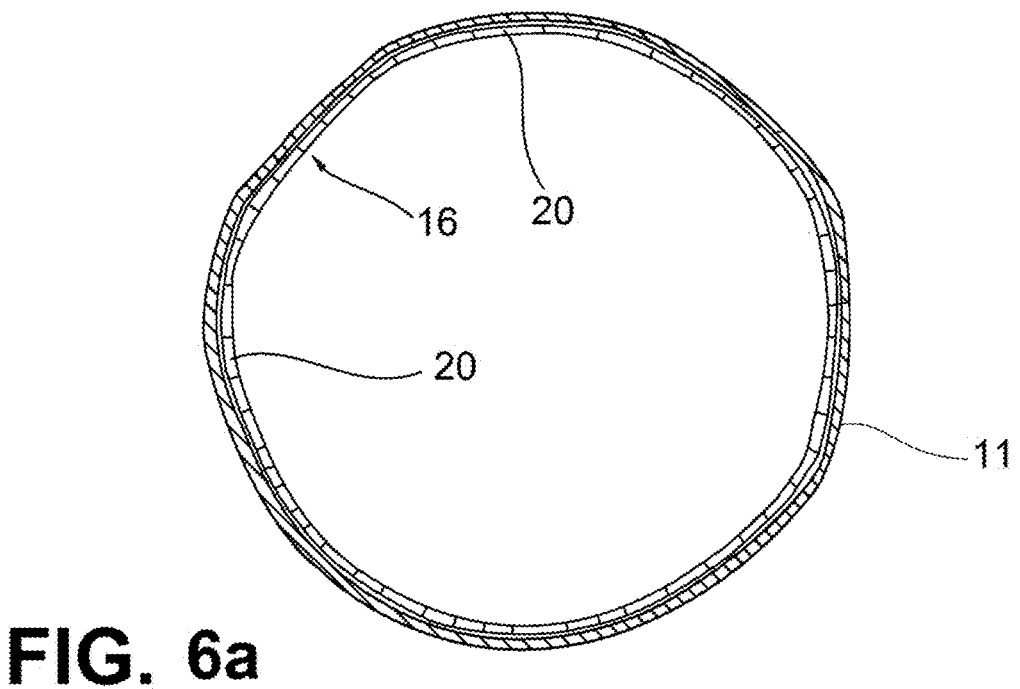
FIG. 6a is a sectioned view of a prosthesis in which its lining is deflated, according to one embodiment of the invention.

FIG. 6a is a sectioned view of a prosthesis in which its lining is deflated, according to one embodiment of the invention.

Figure 6B:
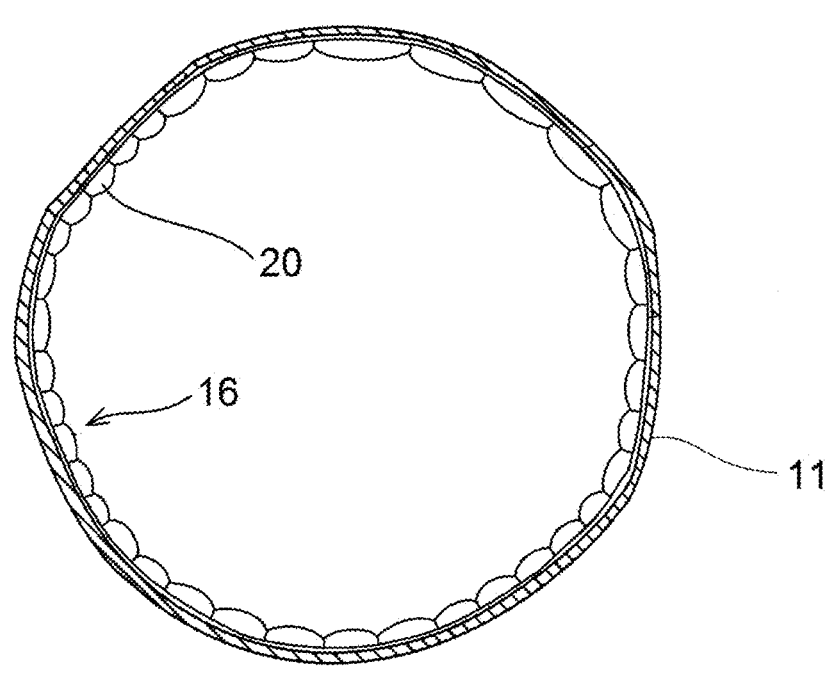
FIG. 6b is a sectioned view of a prosthesis in which its lining is inflated, according to one embodiment of the invention.

FIG. 6b is a sectioned view of a prosthesis in which its lining is inflated, according to one embodiment of the invention.

The lining comprises inflatable cells 20, connected each other by air passages. Thus, when a residual limb of a user is disposed inside the lining, as the lining is inflated its grip to the user's limb increases.

The user may stop the inflating operation by the remote control.

When the user feels the grip of the lining is getting loose, he may increase the air pressure inside the lining by the remote control device. Additionally or alternatively, the controller may increase the air pressure inside the inflatable lining.

The cells inside the lining prevent from the air inside the lining to move from a side of the lining in which the pressure is "high" to another side of the lining in which the pressure is "low". Lack of cells will cause the leg not to be fixed inside the pillow, so the user's posture will not be stable. The cells provide to the lining softness along with posture.

For allowing inflating all the cells simultaneously, the lining's cells may be interconnected.

Figure 6C:
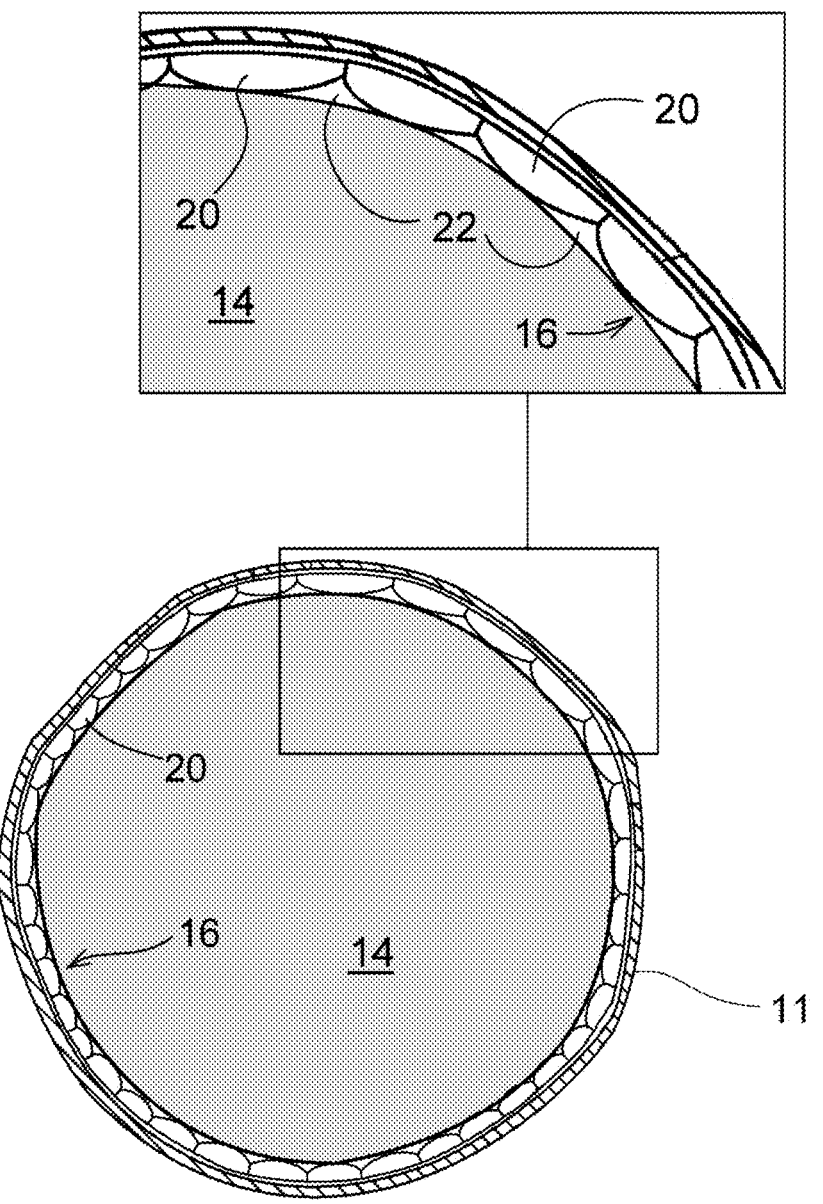
FIG. 6c is a sectioned view of a prosthesis in which its lining is inflated, and a zoomed view thereof, according to one embodiment of the invention.

FIG. 6c is a sectioned view of a prosthesis in which its lining is inflated, and a zoomed view thereof, according to one embodiment of the invention.

The lining 16 includes between fifteen to sixty longitudinally inflatable cells 20, with each of the cells located immediately adjacent to two other cells so that no intervening element is provided other than a common boundary between two such adjacent cells. When the inflatable cells 20 are inflated, a gap 22 is created between any two adjacent cells. In the area of the gap 22, the lining 16 does not press on the stump 14. This fact allows easier blood flow in the stump at the gap 22 areas than in the areas of the inflated cells are in contact with the stump.

From the experiments conducted by the inventors, they came to the conclusion that along the circumference of the stump there should be between 15 and 60 vertical inflatable cells, adjacent to each other so that no object separates them.

When there are less than 15 inflatable cells in a lining, the number of spaces 22 along the circumference of the stump is "small", so the blood flow in the stump is less free. When there are more inflatable cells than 60, although there are "a lot" of spaces 22, they are small, so that even in this case the blood flow in the stump is less free.

The longitudinal direction of the inflatable cells corresponds to the longitudinal direction of blood vessels in the stump, so that the spaces 22 between adjacent inflatable cells allow more blood vessels not to be exposed to the pressing inflatable cells. In the case of horizontal orientation of inflatable cells, they exert pressure on the vertical blood vessels, thus interfering with blood flow in the blood vessels.

Figure 7:
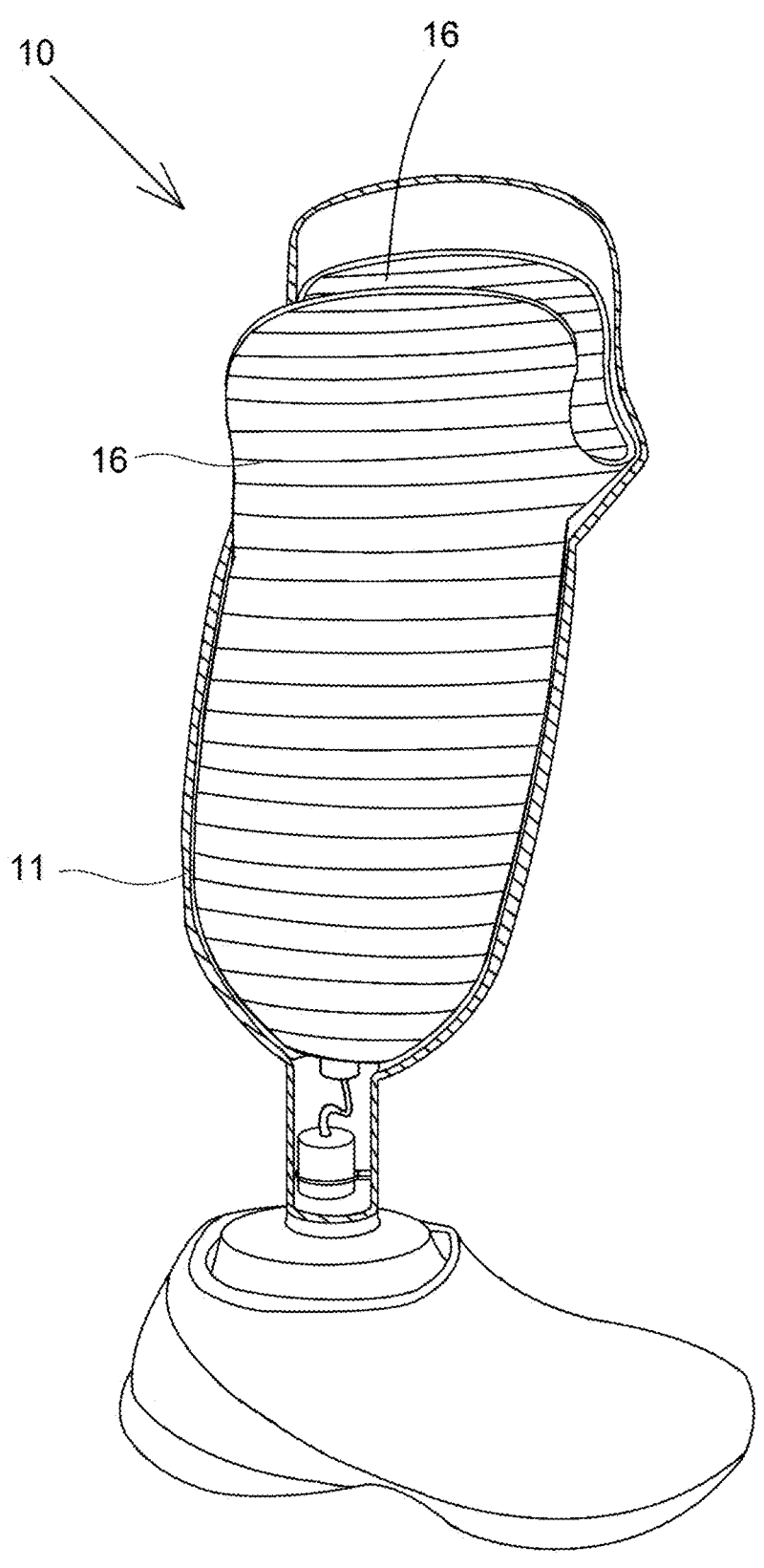
FIG. 7 schematically illustrates a prosthesis, according to one embodiment of the invention.

FIG. 7 schematically illustrates a prosthesis, according to one embodiment of the invention.

In this figure the socket 11 is sectioned in order to reveal the inner structure.

In addition, the lining 16 is shown in the figures herein as transparent, in order to show its cells.

As illustrated, the lining 16 comprises latitudinal cells.

Referring back to FIG. 4, the lining 16 comprises longitudinal cells 20. However, it should be noted that the cells may be latitudinal, latitudinal as well and also in a crisscross order. There is an air passage (not illustrated in these figures) between each of the adjacent cells for allowing inflating and deflating the cells simultaneously by a single pump.

It should be noted that producing a lining with crisscross cells is more complicated than a lining having longitudinal or latitudinal cells.

Figure 8:
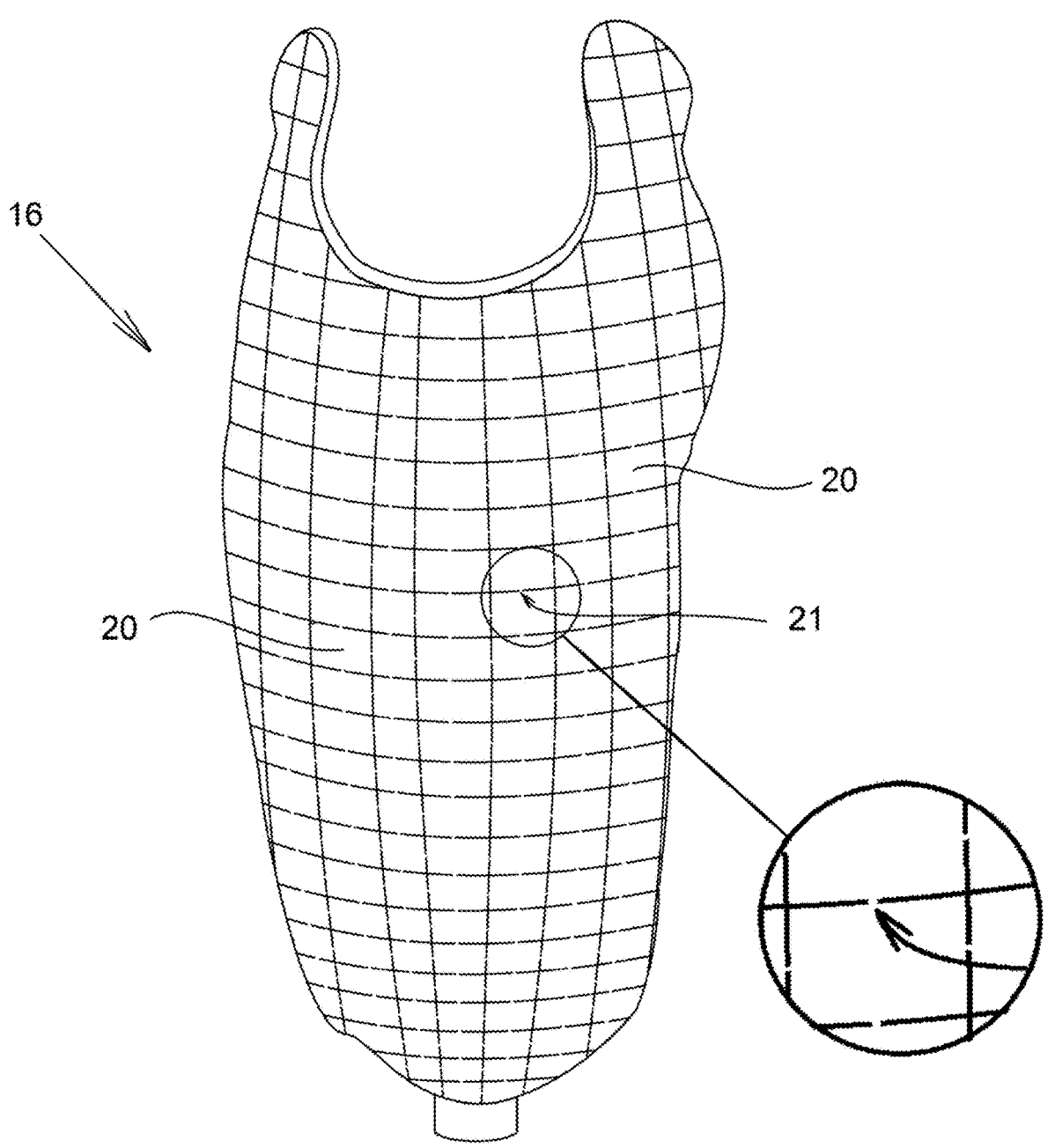
FIG. 8 schematically illustrates a lining of a prosthesis, according to one embodiment of the invention.

FIG. 8 schematically illustrates a lining of a prosthesis, according to one embodiment of the invention.

The lining is illustrated from a front view.

Each inflatable cell 20 of the lining comprises an air passage 21 with its adjacent cells.

In this example, the inflatable cells 20 are in a crisscross order.

It should be noted that the prosthesis may be oriented to above-the-knee as well as to under-the-knee, and actually to any limb including hand.

In the figures and/or description herein, the following reference numerals (Reference Signs List) have been mentioned:

numeral 10 denotes a prosthesis;
numeral 11 denotes a socket of a prosthesis;
numeral 12 denotes a prosthetic foot of a prosthesis;
numeral 13 denotes a joint pipe connecting a socket 11 with a prosthetic foot 12;
numeral 14 denotes a foot stump;
numeral 15 denotes a sock;
numeral 16 denotes a lining;
numeral 17 denotes a remote control device;
numeral 18 denotes wireless communication;
numeral 19 denotes a pump assembly;
numeral 20 denotes an inflatable cell;
numeral 21 denotes an air passage in a cell of a lining; and
numeral 22 denotes a gap created between any two adjacent inflatable cells 20.

In the description herein, the following references have been mentioned: U.S. Pat. No. 5,405,405A, EP2327378A1.

The foregoing description and illustrations of the embodiments of the invention has been presented for the purposes of illustration. It is not intended to be exhaustive or to limit the invention to the above description in any form.

Any term that has been defined above and used in the claims, should to be interpreted according to this definition.

The reference numbers in the claims are not a part of the claims, but rather used for facilitating the reading thereof. These reference numbers should not be interpreted as limiting the claims in any form.

What is claimed is:

1. A limb prosthesis, comprising:
a socket comprising an inner cavity configured for disposal therein of a limb stump of a user;
a means for changing an inner diameter of said inner cavity by a remote control, wherein said means for changing said inner diameter comprises:
a lining (16) disposed within said cavity, said lining comprising between fifteen and sixty of only longitudinal inflatable cells, each cell comprising an inwardly-facing surface having a convex curvature, wherein each of said cells is situated immediately adjacent to two other of said cells such that no intervening element aside from a shared border is provided between two such immediately adjacent cells
wherein all of said inflatable cells are configured to inflate simultaneously towards a limb stump disposed in said prosthesis, wherein inflation or deflation of said inflatable cells changes said inner diameter of said cavity, providing an adjustable space between said cells and said limb stump, thereby diminishing blood flow blockage in the limb stump, and wherein upon inflation of said inflatable cells, a gap is generated between said inwardly-facing surfaces having convex curvature of adjacent said cells; and
a pump assembly (19), for inflating and deflating air in the inflatable lining (16) to a desired air pressure set by a user or by a controller,
wherein said remote control (17) being in data communication with said pump assembly (19), for instructing said pump assembly to inflate or deflate said lining (16) to said desired air pressure.

2. The limb prosthesis according to claim 1, further comprising a pressure sensor and a controllable valve, for allowing inflating and deflating said lining (16) to a desired pressure.

3. The limb prosthesis according to claim 1, further comprising a circuitry adapted to retain constant pressure in said lining.

4. The limb prosthesis according to claim 1, wherein said remote control (17) is a smartphone, thereby allowing a user to change the pressure of the lining without attracting attention of nearby individuals.

5. The limb prosthesis according to claim 1, wherein said data communication is wired.

6. The limb prosthesis according to claim 1, wherein said data communication is wireless.

7. The limb prosthesis according to claim 1, further comprising means for manually deflating said lining, thereby allowing deflating said lining in the case of an operational fault.

8. The limb prosthesis according to claim 1, wherein said means for changing said inner diameter of said socket of said limb prosthesis by a remote control are pneumatic.

9. The limb prosthesis according to claim 1, wherein said means for changing said inner diameter of said socket of said limb prosthesis by a remote control are mechanical.

10. The limb prosthesis according to claim 1, wherein said pump assembly (19) is disposed in a joint pipe (13) connecting said socket (11) with a prosthetic foot (12).

11. The limb prosthesis according to claim 1, wherein said pump assembly (19) is disposed in a prosthetic foot (12) of said limb prosthesis.

12. The limb prosthesis according to claim 1, further comprising a controller configured to detect changes in stump volume and dynamically adjust the pressure within the inflatable lining to maintain fit and comfort.

13. The limb prosthesis according to claim 1, wherein when the stump of said user is disposed in the limb prosthesis, a longitudinal direction of said longitudinal inflatable cells corresponds to a longitudinal direction of blood vessels in the stump of said user.

\* \* \* \* \*